United States Patent [19]
Rothenberg

[11] Patent Number: 5,454,375
[45] Date of Patent: Oct. 3, 1995

[54] PNEUMOTACHOGRAPH MASK OR MOUTHPIECE COUPLING ELEMENT FOR AIRFLOW MEASUREMENT DURING SPEECH OR SINGING

[75] Inventor: Martin Rothenberg, Syracuse, N.Y.

[73] Assignee: Glottal Enterprises, Syracuse, N.Y.

[21] Appl. No.: 141,162

[22] Filed: Oct. 21, 1993

[51] Int. Cl.$^6$ .................................................. A61B 5/087
[52] U.S. Cl. ........................... 128/716; 128/720; 128/725; 128/727; 73/23.3
[58] Field of Search ............................... 128/716, 720, 128/725, 727, 730, 201.19, 201.17, 206.21, 206.28; 73/23.3, 262

[56] References Cited

U.S. PATENT DOCUMENTS

| | | | |
|---|---|---|---|
| 3,570,474 | 3/1971 | Jonson | 128/694 |
| 3,857,385 | 12/1974 | Hampl | 128/720 |
| 4,071,110 | 1/1978 | Payne | 128/201.19 X |
| 4,259,967 | 4/1981 | Vooren et al. | 128/720 |
| 4,539,983 | 9/1985 | Angell | 128/201.19 |
| 4,844,085 | 7/1989 | Gattinoni | 128/720 |
| 4,989,456 | 2/1991 | Stupecky | 128/725 X |
| 5,107,798 | 12/1992 | Riker | 128/725 |
| 5,111,827 | 5/1992 | Rantala | 73/23.3 |
| 5,195,528 | 3/1993 | Hok | 128/716 |
| 5,211,180 | 5/1993 | Wright et al. | 128/725 |
| 5,279,163 | 1/1994 | D'Antonio et al. | 128/725 X |

OTHER PUBLICATIONS

Baken, R. J., Ph.D. "Clinical Measurement of Speech and Voice," 1987, pp. 284–295.
Beranek, Leo L., "Acoustics," pp. 65, 128–129, 130–31.
Rothenberg, M. "A new inverse–filtering technique for deriving the glottal airflow waveform during voicing", *J. Acoust. Soc. Amer.*, 1973, vol. 53, No. 6, pp. 1632–1645.
Rothenberg, M. "Measurement of Airflow in Speech", *J. Speech and Hearing Research*, Mar., 1977, vol. 20, No. 1, pp. 155–176.
Nagashima Medical Instruments Co., Ltd. brochure, "Phonatory Function Analyzer PS–77H", two pages.
Kay Elemetrics Corp. brochure, "Air–Flow Measurement System" for Aerophone II, one page.

*Primary Examiner*—Lee S. Cohen
*Assistant Examiner*—Brian L. Casler
*Attorney, Agent, or Firm*—Fulbright & Jaworski

[57] ABSTRACT

A pneumotachograph mask or mouthpiece coupling element may reduce the distortion and muffling of the voice otherwise caused by a mask or mouthpiece when measuring the low-frequency components of a volume-velocity of oral or nasal airflow during speech or singing. This improved performance is accomplished by separating the low-frequency components to be measured from the higher frequency or acoustic components by an acoustic filter. The filter passes much of the acoustic energy through the walls of the mask or mouthpiece at a location or locations close to the face. The lower frequency airflow components are funneled by the mask or mouthpiece coupling element through an airflow-measurement transducer. The acoustic filtering can be implemented by a membrane, or array of membranes, in the wall of a chamber located close to, or formed as part of, the mask or mouthpiece. An optional inertive-impedance-forming constriction may be placed in the flow pathway between the chamber and the airflow transducer to provide additional acoustic filtering. By making the acoustic filtering process sufficiently thorough, the low-frequency components funneled by the mask or mouthpiece to the transducer contain none of the momentary reversals in flow direction that normally occur during egressive voice production. The mask or mouthpiece coupling element may be used with a transducer that only measures unidirectional flow. Additional acoustic filter elements may be added in the flow path to the transducer and may further reduce the acoustic energy reaching the transducer.

33 Claims, 4 Drawing Sheets

PNEUMOTACHOGRAPH MASK OR MOUTHPIECE COUPLING ELEMENT FOR AIRFLOW MEASUREMENT DURING SPEECH OR SINGING

BACKGROUND OF THE INVENTION

1. Field of the Invention

The invention relates to a pneumotachograph mask or mouthpiece coupling element for airflow measurement, and more particularly, to a pneumotachograph mask or mouthpiece coupling element for use with a pneumotachograph during speech or singing.

2. Description of the Related Technology

Measurements of the volume-velocity of the airflow exiting the mouth or the nose during speech or singing are useful in evaluating the efficiency of voice production and measuring the pattern of valving of the airflow stream by the articulators. Systems for measuring this airflow, often referred to as pneumotachographs, can be categorized by their frequency response.

The acoustic or audible voice frequencies begin at about 50 Hz. (The threshold of audibility is somewhat lower 15 to 20 Hz.) When measuring only the average airflow in each of a sequence of speech sounds (and not detailed variations within each speech sound), the upper frequency limit is determined by how fast the articulatory organs can produce the sounds. This limit is about 10 Hz to 15 Hz, as witnessed by the way children count seconds using the sequence "One Mississippi, Two Mississippi, etc." (Mississippi has eight speech sounds.) When measuring airflow in an artificially prolonged vowel sound (as "ahhh"), a system frequency response limitation even lower, say 2 or 3 Hz, is sufficient.

Airflow measurement systems restricted to frequencies below about 20 Hz may determine the rate of lung deflation, the overall aerodynamic efficiency of the voice source, and may measure articulatory valving patterns, as during articulation of consonants in which there are sudden changes in flow or an onset or offset of voice.

On the other hand, to measure the details of the individual repetitive pulses of airflow making up the voice, a good frequency response to at least about 1000 Hz is required. This frequency response is needed to accurately capture the voice fundamental frequency component, which is generally in the range of 100 to 300 Hz, and at least 3 or 4 harmonics, in order to adequately define the pulse wave shape.

For the purpose of describing the invention, one need only differentiate between systems measuring low, principally subsonic, frequencies (below about 20 Hz) and systems which also measure the higher, acoustic frequencies (well above 20 Hz).

Early devices used to measure the low frequency airflow, as well as some current commercial devices, are adaptations of methods used for measuring non-speech respiratory airflow in breathing. In these systems, a solid-walled pneumotachograph mask with an airtight seal to the face is held over the subject's mouth, nose or the combined mouth and nose. Alternatively, the subject breathes through a mouthpiece having an airtight seal to the lips while the nose is held closed.

The mask or mouthpiece funnels the air stream through a volume-flow measurement transducer, such as an intervening tube of some convenient length that need only be much less than a wavelength at the highest frequency to be measured. (A wavelength at 20 Hz is roughly 50 feet.)

Such systems have an inherently limited ability to measure the energy at higher, acoustic frequencies, due to the resonances and other acoustical properties of the mask or tube used to funnel the airflow. These measurement limitations are present even if the flow transducing mechanism is capable of tracking fast variations. This frequency response limit constrains the system from measuring the faster variations of airflow, which occur during the release of a stop consonant or during the individual airflow pulses produced by the voice source.

These methods, i.e., funneling methods, may also have a number of disadvantages, when measuring low frequency airflow. Such disadvantages are present with masks or mouthpieces constructed according to the prior art, when the system is used during speech or singing, as opposed to breathing. The invention is directed toward solving the following problems:

(1) The mask and tube become, in effect, part of the acoustical system formed by the mouth and pharynx and thus alter the vowel or consonant being formed. The resulting change in vocal tract acoustics can include a change in the airflow variables being measured and a change in the quality of the sound produced. For brevity, these changes in the nature of the voice may be referred to as voice distortion.

(2) The mask and tube block or muffle the voice wave transmitted to the surrounding air, so the speaker or a clinician making the measurements may have a greatly distorted perception of the loudness and quality of the voice being produced. This effect may be referred to as voice muffling.

(3) Transducers that measure only unidirectional flow, such as hotwire anemometers and certain mass-flow transducers, cannot be directly employed, even when measuring only the slowly-varying or average egressive airflow during speech or singing. Unidirectional flow measuring transducers are disadvantageous with funneling methods because the voice, unlike the airflow in normal breathing, contains strong high frequency oscillations. When the high frequency oscillations of the voice are stronger than the average airflow, momentary reversals in the instantaneous airflow may result. Thus, the flow transducer in a conventional funneling measurement system must be able to transduce these flow reversals (ac flow components) even if they are to be eliminated in the final system output signal by some form of low-pass filtering or time-averaging.

One method for eliminating or greatly ameliorating the above problems caused by a funneling mask or mouthpiece is disclosed in "A new inverse-filtering technique for deriving the glottal airflow waveform during voicing," *J. Acoust. Soc. Amer.*, Vol. 53, No. 6, pp. 1632–1645, 1973 by M. Rothenberg, the disclosure of which is expressly incorporated herein. According to this method, a "circumferentially-vented" mask or mouthpiece may be utilized.

The mask or mouthpiece, according to the Rothenberg article, includes a flow resistance element, such as a fine-mesh wire screen, which is used as to convert the flow variable to an air pressure variable. The wire screen may cover openings that are distributed over the surface of either a face mask or a mouthpiece, and are located as close to the mouth as feasible. The wire screen may be combined with a differential pressure transducer that measures the small pressure difference across the screen caused by the airflow.

The circumferentially-vented mask may be used to measure variations in airflow that occur in less than a millisecond (well into the acoustic range) and may cause relatively little distortion and muffling of the voice. A window area of about 10 cm² in a mask chamber covering the mouth and nose should have an impedance of less than about 0.5 cm H₂O/liter per sec, in order to be considered a low impedance acoustic barrier in a typical speech application. More sensitive applications, such as in measurements during singing, might require a window impedance of no more than ½ or ¼ that value. Conversely, larger window areas can have a somewhat higher overall impedance for the same muffling effect.

However, these types of masks cannot be conveniently applied to transduction-methods other than the resistance-pressure method. For example, mass-flow transducers that require a unidirectional flow cannot be used. Further, the presence of a flow resistance element so close to the mouth makes the mask or mouthpiece susceptible to contamination that can change calibration.

For applications that record only the slowly-varying components of the voice airflow, the short response time (or, equivalently, the extended high frequency response) of a circumferentially-vented mask is not a factor. For these low frequency applications there exists a need for a measurement system that does not significantly distort or muffle the voice.

It is also desirable to locate a transduction mechanism at a greater distance from the mouth than the distance typically accommodated by a wire-screen of a circumferentially-vented mask or mouthpiece. There also exists a need for a low frequency system useable with transducers which require a unidirectional flow for proper operation.

SUMMARY OF THE INVENTION

It is an object of the invention to provide a mask or mouthpiece coupling element that funnels low-frequency components into a transducer appropriate for measuring such airflow components, while causing significantly less distortion and muffling of the voice than a funneling-type mask constructed according to the prior art.

It is a further object of the invention to provide a modification for use with a mask or mouthpiece constructed according to the prior art, which results in the prior art mask or mouthpiece having significantly less distortion and muffling of the voice.

It is a still further object of the invention to provide a mask or mouthpiece suitable for use with an airflow transducing system which may only measure airflow that moves in only one direction at all times during the measurement interval.

In accordance with one aspect of the invention, the mask or mouthpiece coupling element may include a housing exhibiting walls defining a chamber, and an input port for directing the airflow from the mouth and/or nose into the chamber. The chamber may be located close to the point of contact between the mask or mouthpiece and the face or mouth, respectively. A significant proportion of the chamber walls may exhibit a thin, flexible membrane or membranes that vibrate freely at frequencies important to the perception of the voice. The membranous walls may also be impervious to the passage of air.

The chamber may also have an exit port configured so airflow from the mouth and/or nose is directed through the exit port to a transducer capable of measuring the low-frequency components of the airflow.

The chamber membranous wall may provide a low acoustic impedance between the chamber interior and the outside air at the audible or acoustic voice frequencies, while providing a high impedance to the low-frequency airflow components to be measured. This low-impedance acoustic path between the mouth and the surrounding outside air minimizes both the distortion and the muffling of the voice caused by the mask or mouthpiece.

Moreover, by absorbing the voice frequencies before they pass to the exit port, and hence to the measurement transducer, the chamber also reduces the amplitude of the voice-frequency components in the airflow passed on to the measurement transducer. The chamber thus forms an acoustic wave filter that shunts the higher or voice frequencies to the surrounding air while passing the lower, generally subsonic frequencies to the measurement transducer.

If the separation of higher and lower frequencies can be made sufficiently complete, the airflow directed to the measurement transducer may only have an egressive direction during the production of a normal voice or singing tone. (This excludes certain rare ingressive speech sounds found in some languages.) With such a near-complete separation of the higher and lower frequencies, a unidirectional-flow transducer can be used. In other words, for a sufficiently complete separation of the higher and lower frequencies to occur, the peak value of the high frequency energy must be less than the minimum value of the low frequency energy.

It is important to thoroughly eliminate the voice frequencies from the chamber exit port when using certain airflow transducers, i.e., unidirectional airflow transducers. According to the invention, two other features should be considered when the invention is used with such airflow transducers.

First, an acoustic impedance element exhibiting a high impedance at voice frequencies and having a reactive component that is inertive in phase may be located within the exit port, or in the airflow pathway between the exit port and the airflow transducer. A constriction in the flow path, i.e., a narrow diameter tube, may function as such an impedance element, though other forms of acoustic impedance can be used. Equivalently, the constriction may be incorporated into the flow path within the flow measurement transducer. Second, the shunt impedance at voice frequencies within the chamber can be minimized by making the chamber volume larger, thus increasing the acoustic compliance of the air volume within the chamber.

The acoustically transparent membranous sections of the chamber wall may be tensioned or tensed to ensure the sections respond as a linear system element to the acoustic pressure variations within the mask, as opposed to membrane movement that is not proportional to chamber pressure. A system responds linearly in the "time domain" when a change in pressure amplitude by a factor K merely changes the displacement by the same factor (i.e. $Kp_i(t)$ causes a displacement $Kd_i(t)$—the waveform shape remains the same). The result of a sum of component pressure waveform is also merely the sum of applying each separately ($p_1(t)+p_2(t)$ causes $d_1(t)+d_2(t)$). In the "frequency domain," linearity means that if $p_3(t)=p_1(t)+p_2(t)$, the displacement waveform $d_3(t)$ can only have Fourier components at the frequencies of the input components $p_1$ and $p_2$. There are no extra "cross modulation" components introduced. If the wall sections are not pretensed to act as a linear system element, the vibration pattern of the film due to a voice pressure pattern may transmit to the surrounding air the buzz sound quality associated with the child's toy known as the kazoo instead of the true voice wave.

A method for tensing the membranous portions of the chamber wall can be added to the device described by the invention. For example, the transparent wall sections may be fabricated from a material such as mylar film or a more elastic material such as latex rubber.

An elastic material such as latex rubber can be pretensed, i.e., stretched, before the material is affixed to the chamber wall. According to the invention, a method for uniformly pretensing membranous wall section includes using two membrane layers and introducing a static positive or negative air pressure between the membrane layers.

DETAILED DESCRIPTION OF THE PREFERRED EMBODIMENT

Figure 1A:
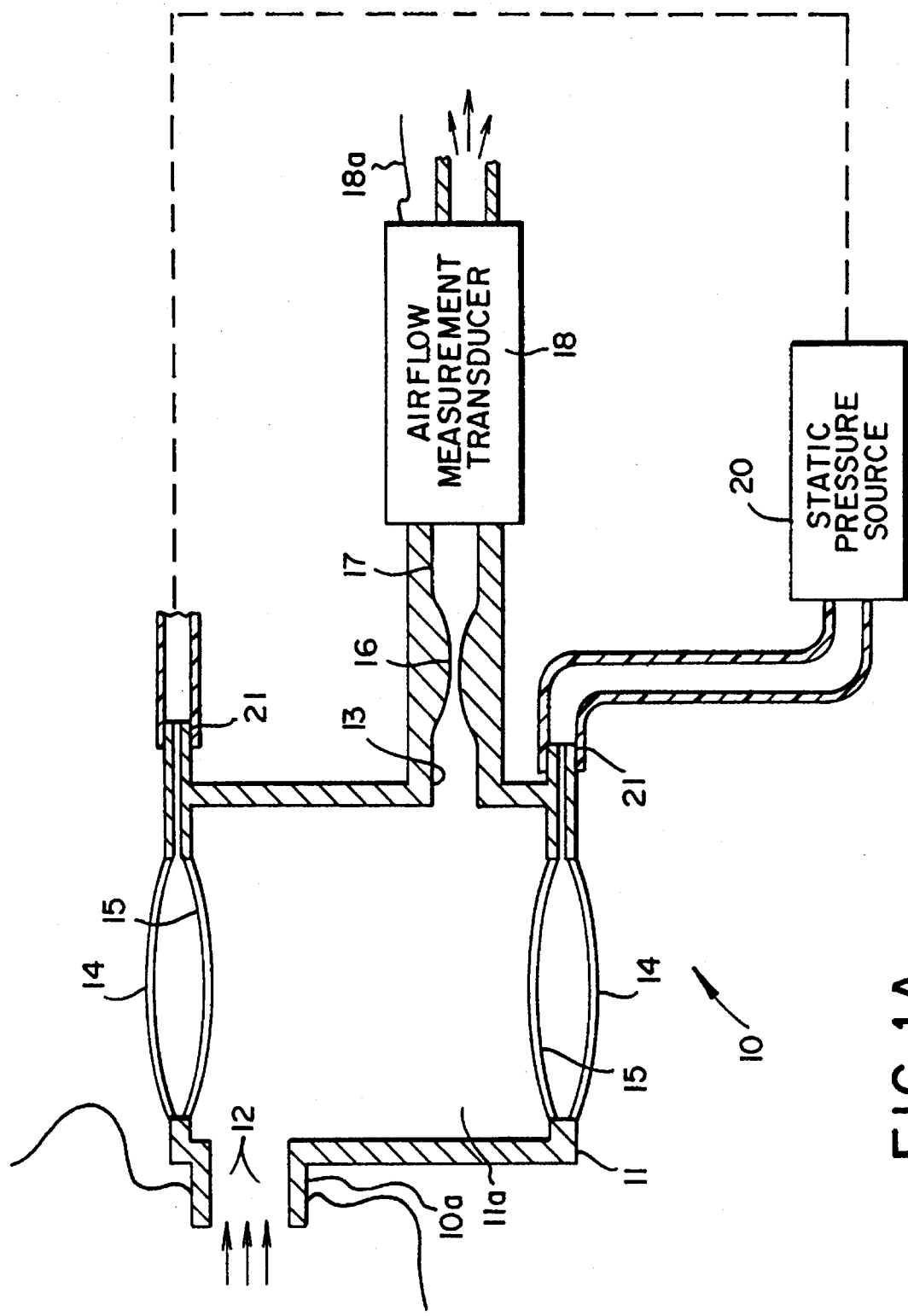
FIG. 1A is a cross-sectional view of a mouthpiece coupling element for measuring the low frequency airflow pattern during speech or singing according to one embodiment of the invention.
Figure 1B:
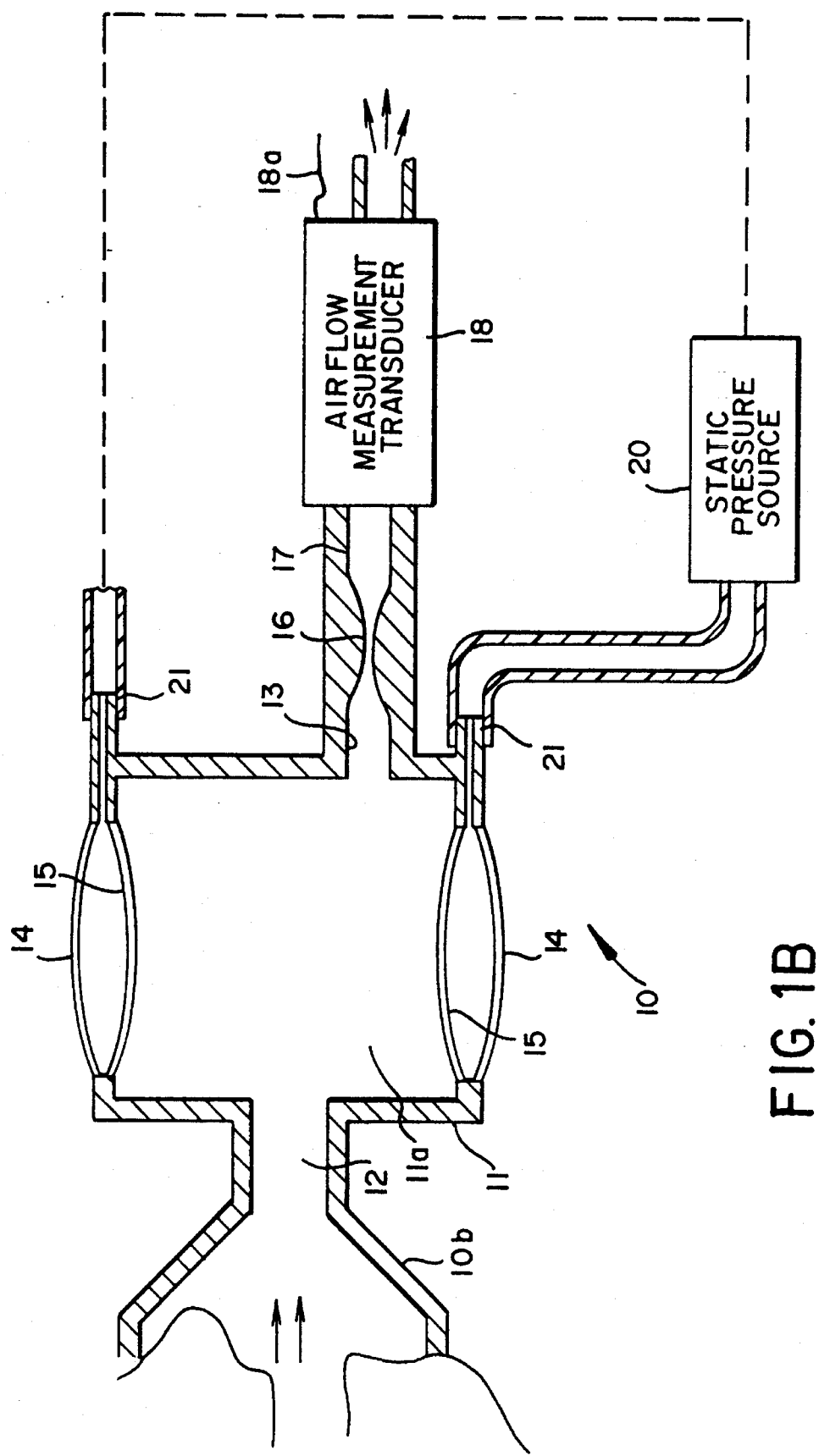
FIG. 1B is a cross-sectional view of a mask for measuring the low frequency airflow pattern during speech or singing according to one embodiment of the invention.

With reference to FIGS. 1A and 1B of the drawing, a pneumotachograph mask or mouthpiece coupling element 10 according to the invention may be used to measure low-frequency components of a volume-velocity of oral and/or nasal airflow. An instantaneous volume-velocity (cubic meters per second), U(t), is defined as the volume flow rate of air passing through a specified channel or orifice having a crossectional area S (square meters). For a flow pattern that has a uniform value of particle velocity (meters per second), u(t), over the specified crossectional area, and a direction of motion perpendicular to the surface in space defined by that area, the volume velocity is equal to u(t) multiplied by S.

FIG. 1A shows a mouthpiece 10a and FIG. 1 B shows a mask 10b according to the invention. A mask may be used to measure low-frequency components of a volume-velocity of oral and/or nasal airflow. In the event that only oral airflow is of interest and the sample of speech or singing being tested does not require lip closure, a mouthpiece can be advantageous.

The pneumotachograph mask or mouthpiece coupler for voice airflow measurement exhibits a housing 11 defining a chamber 11a that may connect an inlet port 12 with an exit port 13. The chamber has a predetermined shape. For example, the chamber may be cylindrical along its horizontal axis or may have flat sides on all aspects. Chamber 11a is advantageously located close to the point of contact between the mask or mouthpiece and the face or mouth, respectively.

According to the preferred embodiment, a large proportion, i.e., a majority, of the wall area of chamber 11a, especially the walls closest to the mouthpiece, are defined by two thin, membranous layers 14, 15. Outer membrane 14 and inner membrane 15 may be configured as thin plastic or rubber film, such as mylar film or latex rubber, respectively.

The membranes or layers 14, 15 may be kept separate and tensed by a small static air pressure or vacuum introduced by a static pressure source 20, such as an electrically operated pump, at one or more inlets 21. The pressure or vacuum introduced between layers 14, 15 should be larger than any instantaneous pressure caused by the voice, so each membrane remains tensed during measurement. It is also contemplated to mechanically tense the membranes, i.e., by strings or springs attached along one end to one of the layers and along the other end to the housing. With a mechanical system for tensing the membranes, it may be possible to replace membrane layers 14, 15 with a single membrane layer.

The airflow pathway through exit port 13 may include constriction 16 to increase the inertance and dissipative resistance in the pathway. Preferably, the constriction is followed by a tube or pathway 17 of some convenient length which connects the mouthpiece coupler or adapter to a transducer 18. The transducer may convert the volume-velocity of the airflow in tube 17 to a convenient form, such as an electrical voltage from an output element 18a. In practice, constriction 16 may be a tube of sufficiently small inside diameter to connect exit port 13 to airflow measurement transducer 18.

Membranes 14, 15 may provide a low acoustic impedance between the chamber interior and the outside air at the audible or acoustic voice frequencies, while providing a high impedance to the low-frequency airflow components to be measured. A sound barrier or membrane has a "low" acoustic impedance if the sound pressure is little reduced or modified in waveshape when passing through the barrier or membrane. In the instant invention, the acoustic impedance of interest for an impermeable membrane would be measured in the frequency range most relevant for voice waveforms, extending maximally from about 50 Hz to 6,000 Hz, and with the range most relevant for voiced speech being about 100 Hz to 3,000 Hz. This low-impedance acoustic path between the mouth and the surrounding outside air minimizes both the distortion and the muffling of the voice caused by the mask or mouthpiece.

Figure 2:
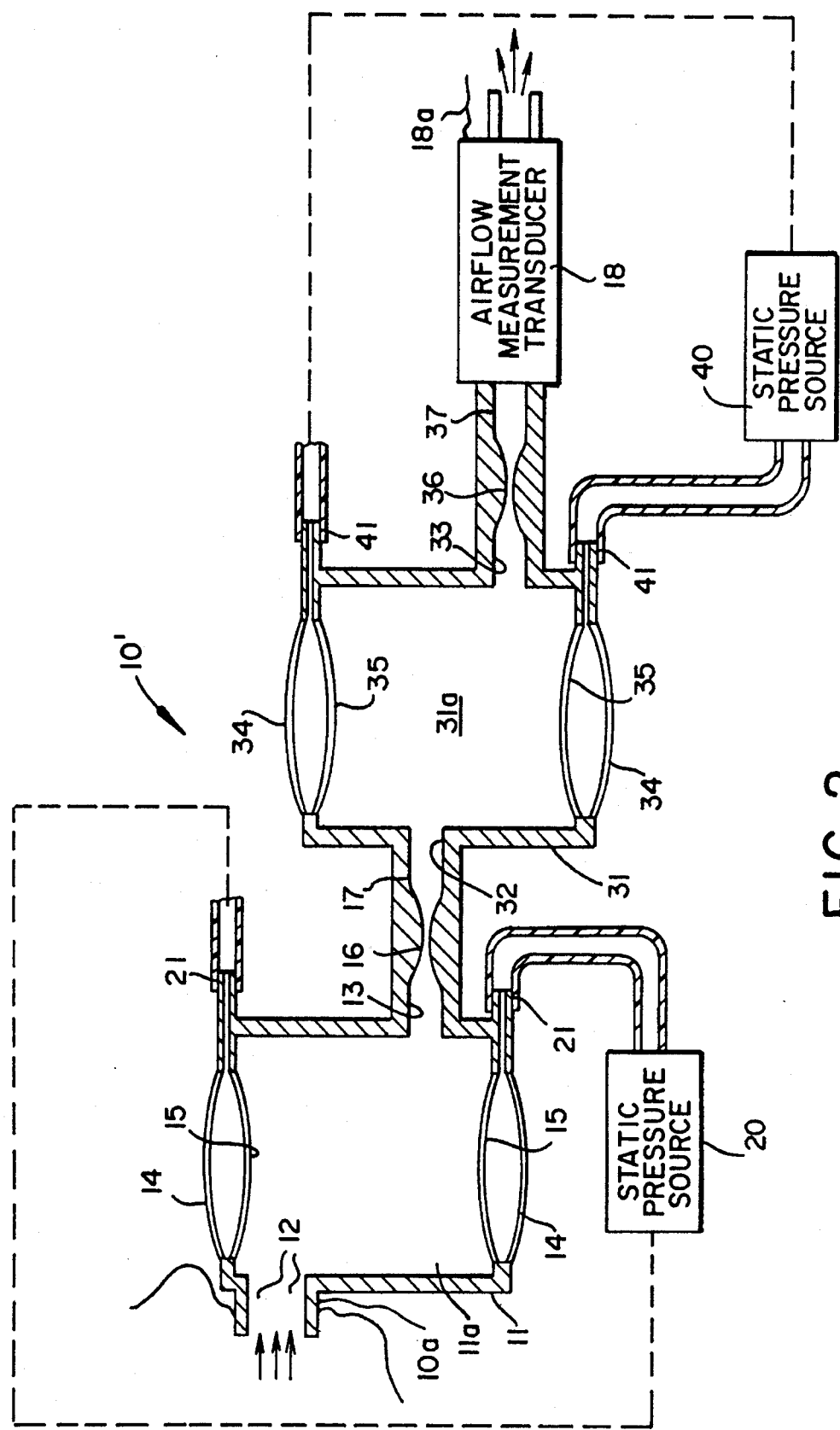
FIG. 2 is a cross-sectional view of a mouthpiece coupling element for measuring the low frequency airflow pattern during speech or singing according a second embodiment of the invention.

FIG. 2 shows a second embodiment 10' of the invention. This embodiment is preferred when using a flow transducer that may only operate with unidirectional flow. As it is contemplated to use the invention with a variety of airflow transducers, i.e., a differential pressure transducer, a hotwire anemometer, a rotating wheel, or a mass-flow transducer on an integrated circuit chip, problems associated with certain transducers, such as unidirectional flow transducers, must be addressed.

As one of ordinary skill in the art may appreciate, a differential pressure transducer can be combined with a linear flow resistance to provide an excellent linear characteristic relating pressure and flow. In other words, the instaneous measured pressure can be made substantially linearly proportional to the instantaneous measured airflow for both negative and positive values of airflow.

In contrast, a simple hot-wire anemometer (which registers the cooling effect of airflow passing approximately perpendicular to an electrically heated wire) is not sensitive to the direction of airflow, as the cooling effect of the flow is independent of flow direction—thus, it is a unidirectional flow transducer. Further, since the cooling of the hot-wire is not linearly related to the magnitude of the airflow, unwanted higher frequency oscillations in the flow pattern can disadvantageously alter the desired measurements of the lower frequency components of the airflow. Because of these factors, when using a unidirectional flow transducer, such as a simple hot-wire anemometer, the embodiment of the invention as set forth in FIG. 2 is preferred.

Pneumotachograph mask or mouthpiece coupler 10', as set forth in FIG. 2, may include a housing 11 exhibiting walls defining a chamber 11a, and an input port 12 for directing the airflow from the mouth and/or nose into the chamber. The chamber may be located close to the point of contact between the mask or mouthpiece and the face or mouth, respectively. A significant proportion of the chamber walls may exhibit thin, flexible membranes 14, 15 that vibrate freely at frequencies important to the perception of the voice, and may also be impervious to the passage of air.

The chamber may also exhibit an exit port 13 configured so airflow from the mouth and/or nose is directed through the exit port to transducer 18, which is capable of measuring the low-frequency components of the airflow.

By absorbing the voice frequencies before they pass to the exit port, and hence to the measurement transducer, the chamber 11a also reduces the amplitude of the voice-frequency components in the airflow passed on to the measurement transducer. Advantageously, the chamber is configured as an acoustic wave filter that shunts the higher or voice frequencies to the surrounding air while passing the lower, generally subsonic frequencies to the measurement transducer.

If the separation of higher and lower frequencies is made sufficiently complete, i.e., such that the peak value of the high frequency energy is less than the minimum value of the low frequency energy, the airflow directed to the measurement transducer will only have an egressive direction during the production of a normal voice or singing tone. With such a near-complete separation of the higher and lower frequencies, a unidirectional-flow transducer can be used. According to the invention, additional acoustic filter elements may be located in the pathway formed by tube 17 between constriction 16 and transducer 18 to separate the higher and lower frequencies.

The additional acoustic filter elements may include an additional housing 31, which defines an additional chamber 31a of large volume. The additional chamber 31a may also include an inlet port 32 and an exit port 33 followed by an additional constriction 36. According to this embodiment, it is preferred to have a majority of the wall area of additional chamber 31 defined by outer membrane 34 and inner membrane 35. In addition to constriction 36, an additional tube 37 may be located between the additional chamber exit port and the airflow measurement transducer.

Membranous layers 34, 35 may be kept separate and tensed by a small static air pressure or vacuum introduced by an additional static pressure source 40 such as an electrically operated pump at one or more inlets 41. It is also contemplated to utilize a single source of static pressure, in lieu of plural sources 20, 40. The pressure or vacuum introduced between the layers should be larger than any instantaneous pressure caused by the voice, so each membrane remains tensed during measurement.

Figure 3:
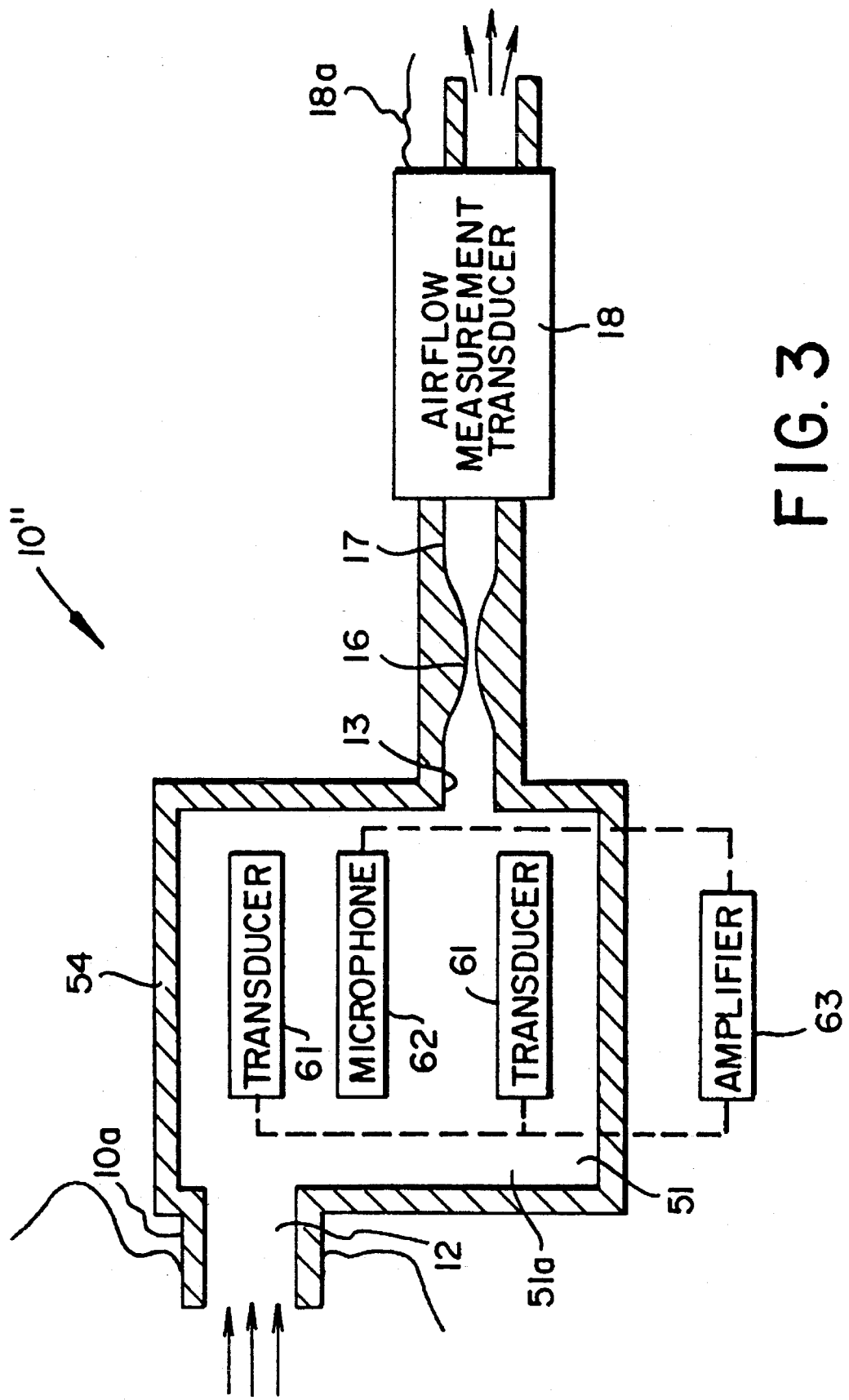
FIG. 3 is a cross-sectional view of a mouthpiece coupling element for measuring the low frequency airflow pattern during speech or singing according a third embodiment of the invention.

FIG. 3 illustrates a third embodiment of the invention. One of ordinary skill in the art may appreciate that the previous embodiments including flexible membranes 14, 15 and flexible membranes 34, 35, each form a passive sound absorption system. In contrast, the pneumotachograph mask or mouthpiece coupler 10" according to the third embodiment may include an active sound absorption system.

According to this embodiment, a housing 51 exhibits at least one chamber wall 54 that defines chamber 51a. It is preferred for an active system to include one or more loudspeaker-type transducers 61 mounted in, or located along, chamber wall 54 of chamber 51. The chamber may include inlet 52 and exit port 53.

Transducers 61 may be driven, through a suitable electrical amplifier 63, by the voltage from a small microphone 62 located within the chamber or along the chamber wall 54. The polarity of the voltage to the loudspeakers may produce an acoustic pressure that cancels the acoustic pressure within the chamber.

The illustrated embodiments are shown by way of example. The spirit and scope of the invention is not to be restricted by the preferred embodiments shown.

What is claimed is:

1. A pneumotachograph comprising:

an airflow transducer;

a coupling element connected to said airflow transducer, said coupling element including walls and defining a hollow chamber;

an inlet port connected to said chamber;

an exit port connecting said chamber to said airflow transducer;

said coupling element walls including a vibratory, flexible, membranous wall section.

2. A pneumotachograph according to claim 1, further comprising:

a mask; said coupling element connecting said mask to said airflow transducer.

3. A pneumotachograph according to claim 2, wherein said mask and said coupling element are integrally connected and define a single element.

4. A pneumotachograph according to claim 1, further comprising:

a mouthpiece; said coupling element connecting said mouthpiece to said airflow transducer.

5. A pneumotachograph according to claim 4, wherein said mouthpiece and said coupling element are integrally connected and define a single element.

6. A pneumotachograph mask or mouthpiece coupling element comprising:

a coupling element housing for connecting a mask or mouthpiece to an airflow transducer, said coupling element housing including walls and defining a hollow chamber;

an inlet port connected to said chamber;

an exit port connecting said chamber to said airflow transducer;

said coupling element housing walls including a wall area defined at least in part by at least one vibratory membrane having low acoustic impedance at voice frequencies.

7. A pneumotachograph mask or mouthpiece coupling element according to claim 6, wherein said at least one vibratory membrane comprises a majority of said coupling element housing wall area.

8. A pneumotachograph mask or mouthpiece coupling element according to claim 6, wherein said at least one vibratory membrane is an elastic, pretensed membrane.

9. A pneumotachograph mask or mouthpiece coupling element according to claim 6, further comprising a membrane-stiffening mechanism connected to said at least one vibratory membrane wherein a membrane vibration and a chamber pressure define a linear relationship.

10. A pneumotachograph mask or mouthpiece coupling element according to claim 9, wherein said membrane-stiffening mechanism is a pressurized fluid source.

11. A pneumotachograph mask or mouthpiece coupling element according to claim 9, wherein said membraneostiffening mechanism allows a positive or negative static fluid pressure between said membranes.

12. A pneumotachograph mask or mouthpiece coupling element according to claim 6, wherein said at least one vibratory membrane includes two membranous layers.

13. A pneumotachograph mask or mouthpiece coupling element according to claim 6, further comprising:
   a flow constriction having a high impedance at voice frequencies and in fluid connection with said housing chamber;
   wherein said housing chamber is an acoustic low pass filter located in an airflow path between a mask or mouthpice and an airflow transducer and configured to reduce the energy in the volume-velocity at voice frequencies.

14. A pneumotachograph mask or mouthpiece coupling element according to claim 13, further comprising:
   an additional housing chamber located in a flow pathway between said inlet port and an airflow transducer and having at least a low impedance at voice frequencies; and
   an additional acoustic element having at least a high inertive impedance at the acoustic voice frequencies; said additional housing chamber configured as a low-pass filter at acoustic voice frequencies, thereby further limiting the voice frequency energy reaching the airflow transducer.

15. A pneumotachograph mask or mouthpiece coupling element according to claim 14, wherein said additional acoustic element is a flow constriction.

16. A pneumotachograph mask or mouthpiece coupling element according to claim 6, wherein said housing chamber is further configured so a majority of the acoustic energy in the volume-velocity passes through walls of the coupling element housing.

17. A pneumotachograph mask or mouthpiece coupling element according to claim 6, further comprising:
   at least one transducer located along said coupling element housing walls; and
   a microphone located along said coupling element housing walls and connected to said at least one transducer.

18. A pneumotachograph mask or mouthpiece coupling element according to claim 17, wherein said at least one transducer is a loudspeaker-type transducer.

19. A pneumotachograph mask or mouthpiece coupling element according to claim 6, wherein said coupling element housing walls include a wall area defined at least in part by a vibratory membrane having low acoustic impedance at voice frequencies, said mask or mouthpiece coupling element further comprising:
   a membraneostiffening mechanism connected to said membrane.

20. A method of measuring low-frequency components of a volume-velocity of oral or nasal airflow comprising the steps of:
   passing the volume-velocity through a chamber of a pneumotachograph;
   filtering at least a portion of acoustic energy in the volume-velocity through a wall of the pneumotachograph chamber;
   passing remaining airflow components, including at least low frequency energy, to an airflow measurement transducer.

21. A method of measuring the low frequency components according to claim 20, further comprising the step of:
   passing the airflow going to the airflow measurement transducer through a constriction in the flow path.

22. A method of measuring low-frequency components according to claim 21, wherein said step of passing remaining airflow components to an airflow measurement transducer further comprises:
   passing the remaining airflow components through an additional pneumotachograph chamber located between the flow constriction and the airflow measurement transducer.

23. A method of measuring low-frequency components according to claim 20 further comprising the step of:
   tensing the wall of the pneumotachograph chamber.

24. A method of measuring low-frequency components according to claim 23, wherein the pneumotachograph chamber wall is a plurality of walls, and said step of tensing the wall of the pneumotachograph chamber further comprises:
   introducing static fluid pressure between the pneumotachograph chamber walls.

25. A method of measuring low-frequency components according to claim 23, wherein the pneumotachograph chamber wall is a plurality of walls, said step of tensing the wall of the pneumotachograph chamber further comprises:
   creating a vacuum between the pneumotachograph chamber walls.

26. A method of measuring low-frequency components according to claim 20 further comprising the step of actuating the transducer located within the pneumotachograph chamber.

27. A method of measuring low-frequency components according to claim 20 further comprising the step of introducing an acoustic pressure into the pneumotachograph chamber to substantially cancel an acoustic pressure of the volume-velocity.

28. A pneumotachograph mask or mouthpiece coupling element comprising:
   a house including walls and defining a hollow chamber;
   a volume-velocity inlet port connected to said chamber; and
   a volume-velocity exit port connected to said chamber;
   said housing walls including at least one vibratory, flexible, membranous wall section.

29. A pneumotachograph mask or mouthpiece coupling element according to claim 28, further comprising a membrane-stiffening mechanism connected to said at least one vibratory, flexible, membranous wall section.

30. A pneumotachograph mask or mouthpiece coupling element according to claim 28, further comprising a flow constriction in fluid communication with said volume-velocity exit port.

31. A pneumotachograph mask or mouthpiece coupling element according to claim 28, wherein said chamber is a first chamber, further comprising a second chamber; and
   a flow constriction connecting said first and second chambers.

32. A pneumotachograph mask or mouthpiece coupling element according to claim 28, further comprising:
   at least one transducer located along said housing walls; and
   a microphone located along said housing walls and connected to said at least one transducer.

33. A pneumotachograph mask or mouthpiece coupling element for use during speech or singing comprising:
- a housing including walls and defining a hollow chamber;
- an inlet port connected to said chamber; and
- an exit port connect to said chamber;
- said chamber configured so acoustic energy and volume-velocity of a voice is separated from lower frequency air flow components and a portion of the acoustic energy passes through walls of the mask or mouthpiece coupling element and remaining airflow components, including at least low frequency energy, pass from said exit port to an air flow measurement transducer.

* * * * *